US008992569B2

(12) United States Patent
Franer et al.

(10) Patent No.: US 8,992,569 B2
(45) Date of Patent: Mar. 31, 2015

(54) INSERTION DEVICE AND METHOD OF USE

(75) Inventors: Paul T. Franer, Cincinnati, OH (US); George Mark Pomeroy, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 2042 days.

(21) Appl. No.: 11/771,609

(22) Filed: Jun. 29, 2007

(65) Prior Publication Data
US 2009/0005800 A1   Jan. 1, 2009

(51) Int. Cl.
| A61B 17/08 | (2006.01) |
| A61B 17/34 | (2006.01) |
| A61B 17/02 | (2006.01) |
| A61B 17/3209 | (2006.01) |
| A61B 17/00 | (2006.01) |
| A61B 17/04 | (2006.01) |
| A61B 17/22 | (2006.01) |
| A61B 17/3211 | (2006.01) |
| A61B 19/00 | (2006.01) |

(52) U.S. Cl.
CPC ......... *A61B 17/3421* (2013.01); *A61B 17/0281* (2013.01); *A61B 17/32093* (2013.01); *A61B 2017/00659* (2013.01); *A61B 2017/0417* (2013.01); *A61B 2017/22038* (2013.01); *A61B 2017/32113* (2013.01); *A61B 2017/3484* (2013.01); *A61B 2019/4805* (2013.01)
USPC ........................................................ 606/215

(58) Field of Classification Search
USPC ......... 600/201, 203, 210, 211, 204, 219, 221; 606/167, 185, 215
See application file for complete search history.

(56) References Cited

U.S. PATENT DOCUMENTS

| 5,111,828 | A | | 5/1992 | Kornberg et al. |
| 6,080,114 | A | * | 6/2000 | Russin .......................... 600/567 |
| 8,216,260 | B2 | * | 7/2012 | Lam et al. ..................... 606/153 |
| 2004/0122456 | A1 | * | 6/2004 | Saadat et al. .................. 606/157 |
| 2004/0260343 | A1 | | 12/2004 | Leclair |

FOREIGN PATENT DOCUMENTS

| WO | WO-0012010 | | 3/2000 |
| WO | WO-2004066854 | | 8/2004 |
| WO | WO-2006037639 | | 4/2006 |
| WO | WO 2006037639 A1 | * | 4/2006 |
| WO | WO-2006060420 | | 6/2006 |

OTHER PUBLICATIONS

International Search Report and Written Opinion dated Aug. 10, 2008 for PCT/US2008/066630.

* cited by examiner

*Primary Examiner* — Gregory Anderson
*Assistant Examiner* — Christina Lauer

(57) ABSTRACT

An insertion device configured to provide access to a treatment site within a body cavity (e.g., an abdominal cavity) is provided herein. In general, the device includes any type of elongate sleeve (e.g., a trocar) having an inner lumen. Further, the device includes a tissue retraction mechanism configured to extend from a distal end of the sleeve wherein the tissue retraction mechanism is configured to securely engage a cavity wall such that in response to a retraction force the mechanism can pull the cavity wall over the distal end of the sleeve thereby positioning the sleeve across the cavity wall. Additionally, various embodiments of a method for providing access to a body cavity are also provided herein.

17 Claims, 8 Drawing Sheets

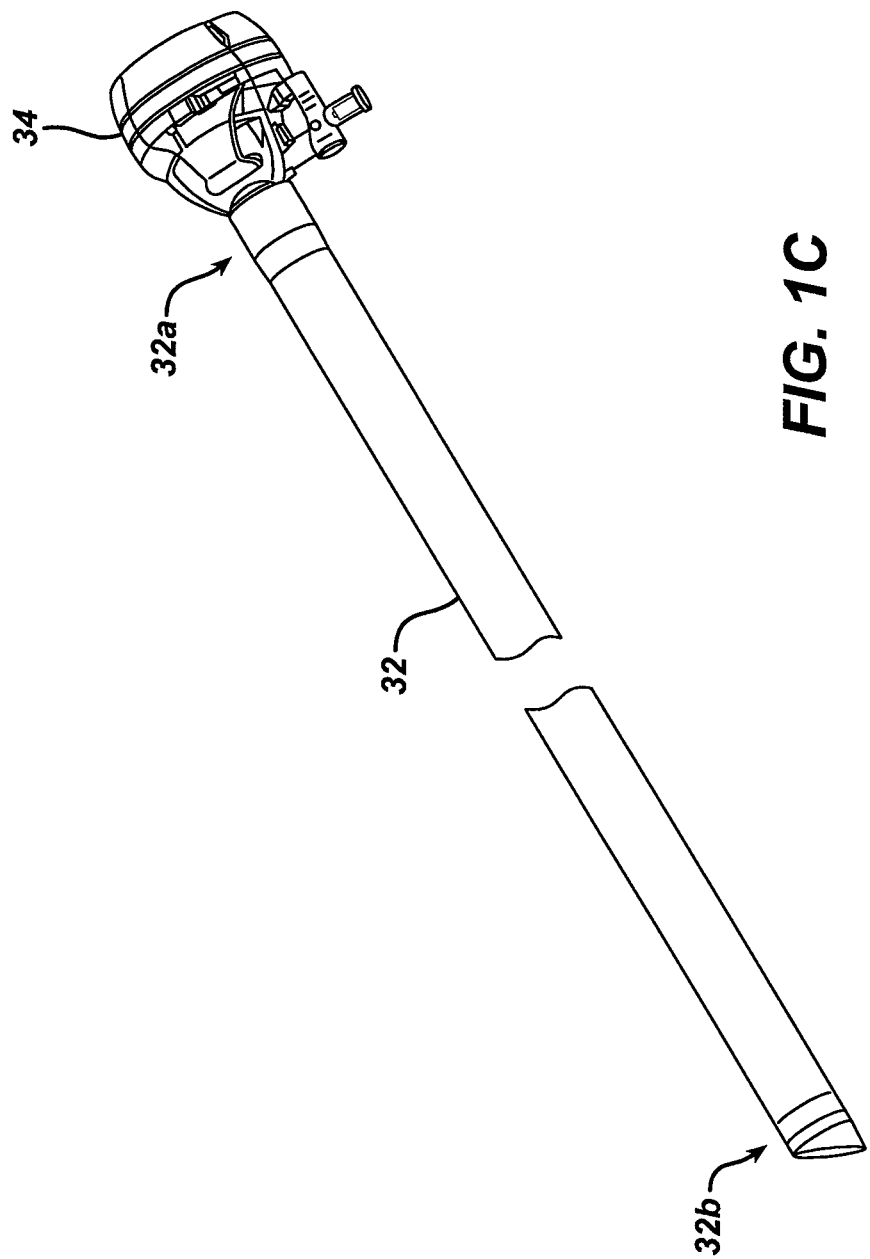

INSERTION DEVICE AND METHOD OF USE

FIELD OF USE

The present invention relates to methods and devices for providing access to a body cavity, in particular for providing access to the abdominal cavity.

BACKGROUND

Various medical procedures require accessing a body cavity via an insertion device such as a trocar assembly. For example, the abdominal cavity contains organs such as the stomach, liver, gallbladder, spleen, pancreas, urinary bladder, and small and large intestines, and is lined with a protective membrane, the peritoneum. As such, to gain surgical access to these above-identified organs, an insertion device must pass through the peritoneum and position a distal portion of the device adjacent the treatment site thereby providing a passageway for the medical professional to the site.

Typically, these procedures require the insertion device to be pushed through the peritoneum following insufflation. Insufflation is the practice of introducing a non-inert gas (e.g., carbon dioxide) into the cavity so as to expand the cavity. As the cavity expands, the peritoneum moves away from the internal organs thereby reducing the potential for injury during delivery of the device. However, this practice is still not entirely desirable. For example, poor control of the insertion device can result in over-insertion of the device thereby resulting in injury. Also, blades are commonly positioned at the distal tip of the insertion device to facilitate driving the device through the tissue of the cavity wall. These blades increase the risk of injury once inside the body cavity. Further, while insufflation allows for added distance between the peritoneum and organs, this working area remains extremely small.

As such, there remains a need in the art for an insertion device capable of being safely introduced to a body cavity.

SUMMARY

Devices and methods are provided herein for the safe and accurate delivery of an insertion device (e.g., a trocar cannula or similar access device) through a body cavity wall to gain access to a treatment site. More specifically, as opposed to pushing the device through the cavity wall, the devices and methods provided herein allow for the cavity wall to be pulled towards and essentially over a distal end of an elongate sleeve thereby substantially eliminating injuries resulting from over-insertion of the device. In general, the device includes a tissue retraction mechanism configured to extend from an opening at a distal end of the elongate sleeve wherein a distal portion of the retraction mechanism can be disposed across the cavity wall and into the body cavity via an insertion needle (e.g., a veress needle). Further, a proximal portion of the mechanism (e.g., a suture or any type of actuation cord) can be slidably disposed within an inner lumen of the sleeve. As a retraction force is supplied to the proximal portion of the retraction mechanism, the distal portion of the retraction mechanism pulls the cavity wall into contact with the elongate sleeve. In use, such force can be supplied until the distal end of the elongate sleeve passes through the cavity wall (essentially, the wall is pulled over the distal end of the sleeve). After insertion of the sleeve through the cavity wall, the retraction mechanism can be withdrawn from the treatment site via the inner lumen of the sleeve thereby leaving the elongate sleeve in position to provide continued access to the treatment site.

Various configurations of the insertion device are provided herein. In one such embodiment, the device includes an elongate sleeve having an inner lumen extending therethrough and a tissue retraction mechanism slidably disposed within the inner lumen and configured to extend from a distal end of the sleeve. Further, the tissue retraction mechanism can include a distal end configured to engage tissue and apply a pulling force to the tissue as the tissue retraction mechanism is moved proximally.

As will be described below, the elongate sleeve can include virtually any type of sleeve or cannula configured to provide access to a treatment site. For example, the elongate sleeve can include an obturator slidably disposed within an inner lumen of an outer cannula. Additionally, the tissue retraction mechanism can also be configured in various manners. For example, the mechanism can include an actuation cord which extends beyond a proximal end of the sleeve. Also, a distal end of the actuation cord can be attached to an elongate member which is configured to engage tissue and apply a pulling force to the tissue as the actuation cord is moved proximally.

Various embodiments of the device can also include a blade configured to facilitate insertion of the device through tissue. In one such embodiment, the device can include a blade disposed within the sleeve. In another embodiment, a blade can be disposed on the distal end of the tissue retraction mechanism. In such an embodiment, the blade can be manipulated from an undeployed state to a deployed state.

In an alternative embodiment, the distal portion of the tissue retraction mechanism can be further configured to deploy as a shield element that adopts the form of an inverted dome in the deployed orientation. As such, the shield element can be configured so as to shield various internal organs from the distal end of the sleeve as the sleeve enters a body cavity.

In another embodiment, a trocar device is provided which includes an elongate sleeve (e.g., an obturator slidably disposed within an outer cannula) having an inner lumen extending therethrough and a retraction element (e.g., a suture or any type of actuation cord) slidably disposed within the inner lumen of the sleeve wherein at least a portion of the retraction element can be configured to extend from a distal end of the sleeve. The trocar device also includes a tissue engagement element coupled to a distal end of the retraction element wherein the tissue engagement element can be configured to apply a pulling force to a tissue as the retraction element is moved in a proximal direction.

The device can include various embodiments of such a tissue engagement element. For example, the tissue engagement element can be configured as an elongate member. In use, the retraction element can be coupled to a mid-portion of the elongate member, and the elongate member can be configured to be oriented perpendicular to a longitudinal axis of the sleeve as the elongate member applies a pulling force to a tissue. Similar to the embodiment discussed above, the tissue engagement element can be include a blade which can be configured to be manipulated from an undeployed state to a deployed state. In another embodiment, the tissue engagement element can be further configured to include a shield element that is configured to be deployed so as to adopt an inverted dome configuration.

Additionally, various methods for providing access to a body cavity are provided herein. In one such embodiment, the method includes delivering a distal end of a retraction mechanism of an insertion device across a body cavity wall. Further, the method includes positioning a portion of the retraction mechanism through an inner lumen of an elongate sleeve wherein the retraction mechanism is configured to be axially movable relative to the sleeve. Additionally, the method can include positioning the distal end of the sleeve adjacent an outer portion of the body cavity wall and retracting the retraction mechanism such the distal end of the retraction mechanism pulls the wall of the cavity toward the distal end of the elongate sleeve. The method can include providing access to any desired body cavity to perform any desired procedure. For example, the method can provide access to the abdomen by passing the device through the peritoneum.

These embodiments, and others, will now be discussed in detail.

BRIEF DESCRIPTION OF THE DRAWINGS

Exemplary embodiments of the invention will be more fully understood from the following detailed description taken in conjunction with the accompanying drawings, in which:

FIG. 1C is a perspective view of the outer cannula of FIG. 1A;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1A:
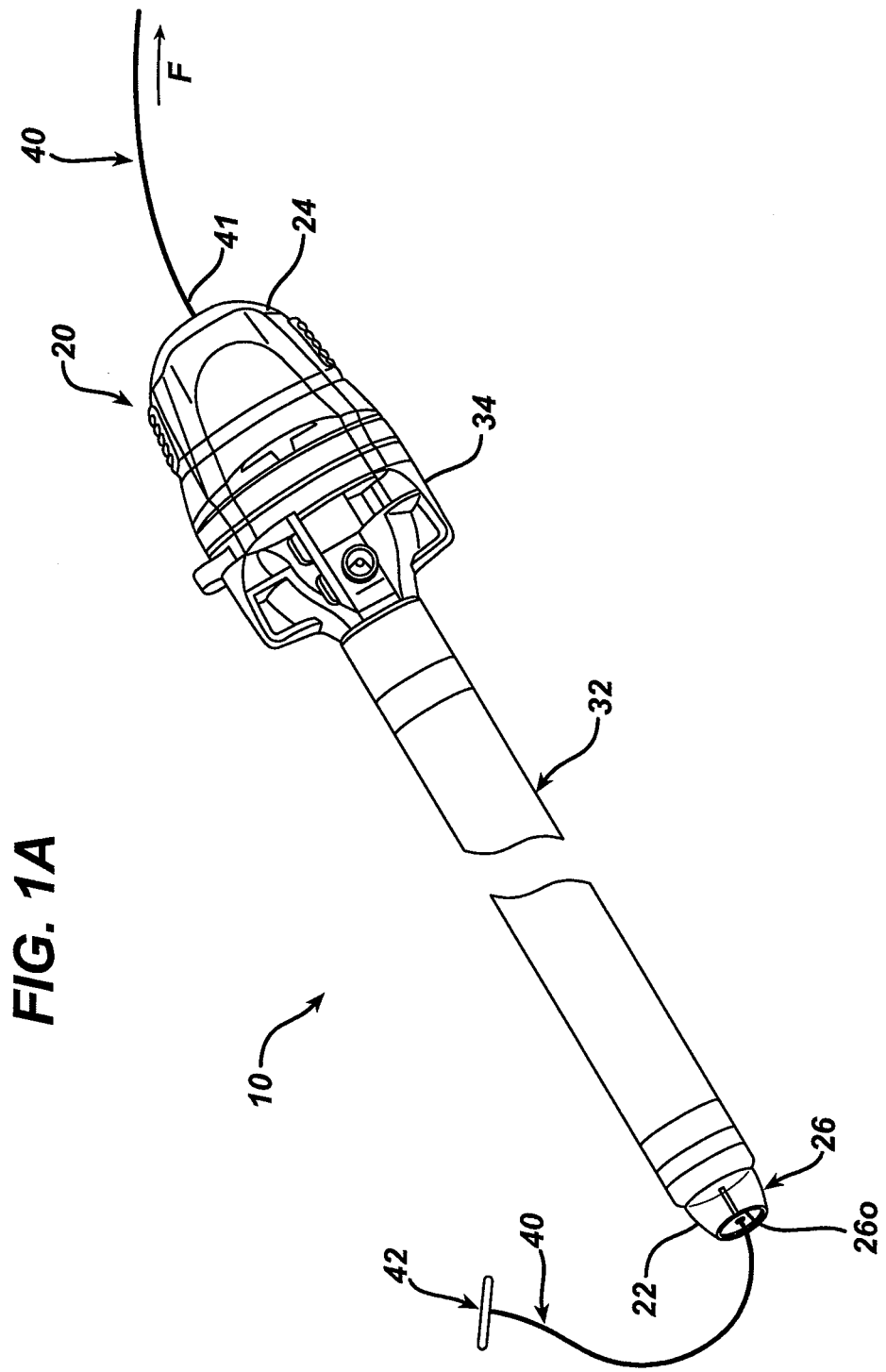
FIG. 1A is a perspective view of one embodiment of an insertion device having an elongate sleeve that partially houses a retraction mechanism and an outer cannula disposed over the elongate sleeve.
Figure 1B:
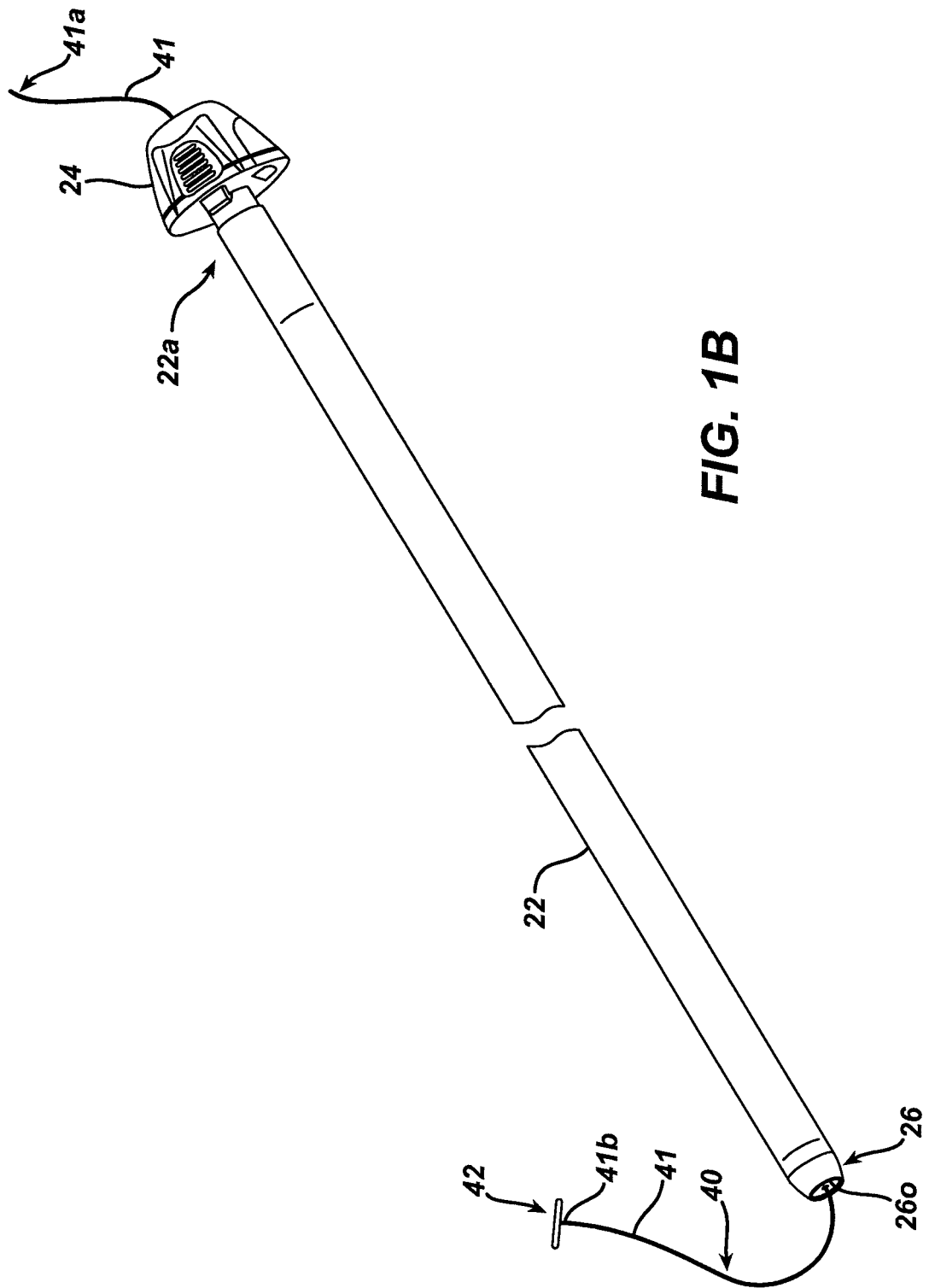
FIG. 1B is a perspective view of the elongate sleeve of FIG. 1A.

Various embodiments of an insertion device, such as a trocar, configured to provide surgical access across a body cavity wall (e.g., the abdominal cavity) are provided herein. FIGS. 1A-1C provide an exemplary embodiment of the device 10. As shown, the device 10 includes an elongate sleeve 22 (alone or in combination with an outer cannula 32) having an inner lumen extending therethrough. The device 10 further includes a tissue retraction mechanism 40 slidably disposed within the inner lumen such that a distal portion of the mechanism 42 can extend from the distal end of the sleeve 26, engage an inner portion of the cavity wall, and be used to pull the cavity wall towards the distal end 26 of the sleeve 22 (e.g., into contact with the sleeve 22 and/or into a portion of the inner lumen through a distal opening 26o of the sleeve 22) as the retraction mechanism 40 is slid proximally (indicated in FIG. 1A by an arrow) by a desired retraction force ("F").

Figure 3A:
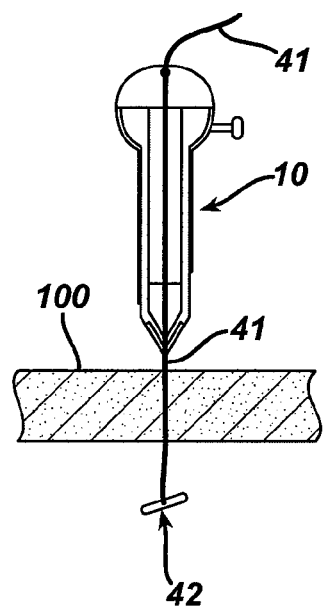
FIG. 3A is a representation of an embodiment of an insertion device having a blade fixedly coupled within an inner lumen of the insertion device.
Figure 3B:
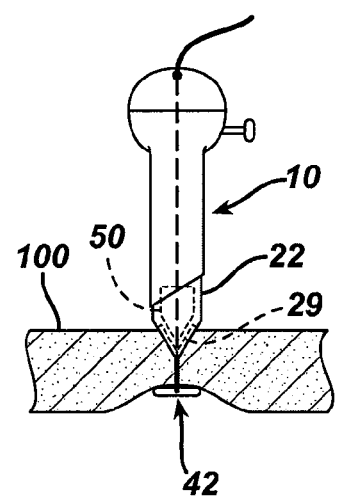
FIG. 3B is a representation of the insertion device of FIG. 3A wherein the retraction mechanism is moved proximally thereby exerting a pulling force on the tissue wall.
Figure 3C:
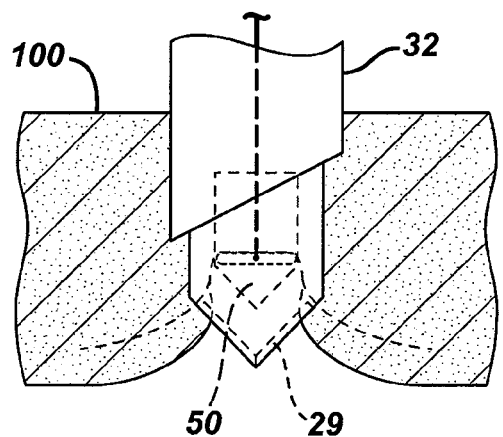
FIG. 3C is a representation of the insertion device of FIG. 3A wherein the tissue wall is pulled within the inner lumen so as to contact the blade.
Figure 4A:
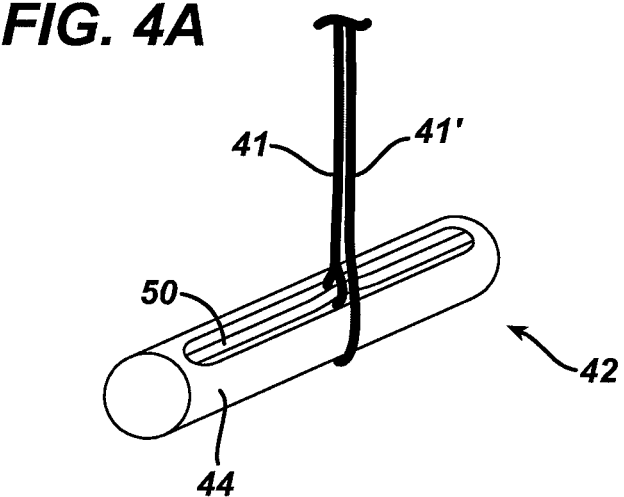
FIG. 4A is a perspective view of an embodiment of a tissue engagement element having a blade in an undeployed state.
Figure 4B:
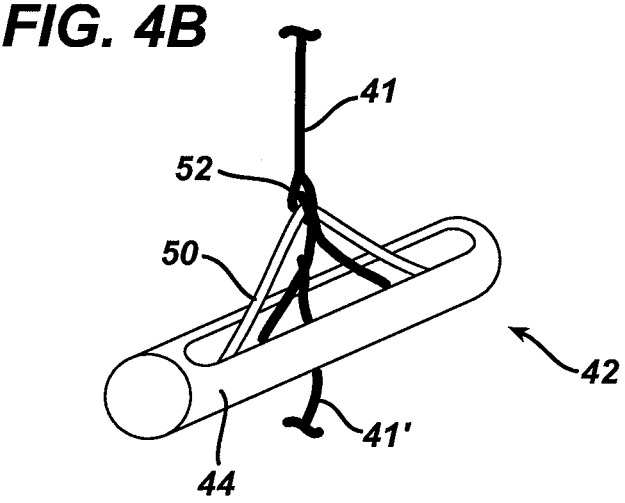
FIG. 4B is a perspective view of the tissue engagement element of FIG. 4A wherein the blade is in a deployed state.
Figure 5A:
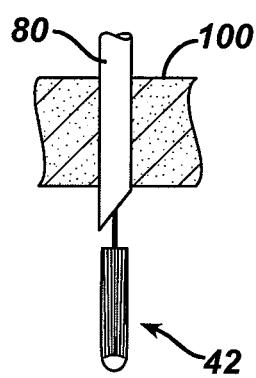
FIG. 5A is a representation of an embodiment of a shield element disposed within a body cavity wherein the shield element is in an undeployed state.
Figure 5B:
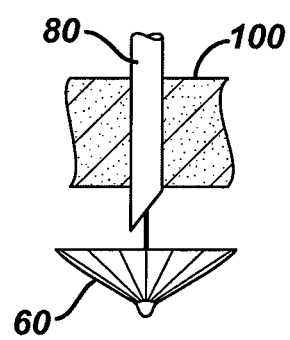
FIG. 5B is a representation of the shield element of FIG. 5A wherein the shield element is in a deployed state.
Figure 5C:
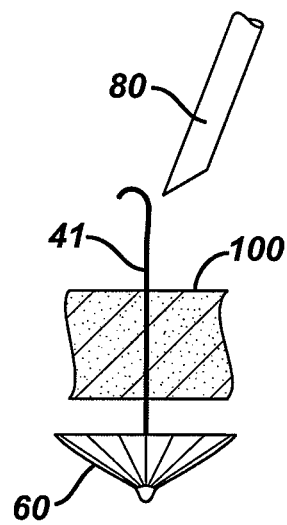
FIG. 5C is a representation of the shield element of FIG. 5A wherein an insertion needle is withdrawn, and the shield element is positioned across the body cavity wall.
Figure 5D:
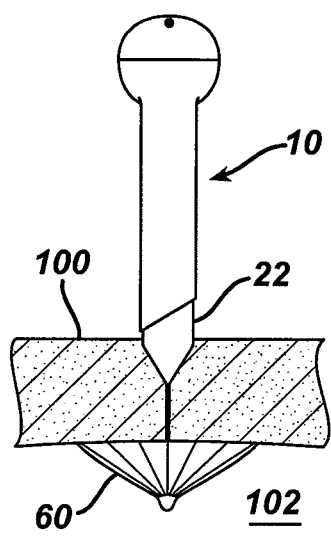
FIG. 5D is a representation of an embodiment of an insertion device receiving a proximal portion of the retraction mechanism of FIG. 5A such that the retraction mechanism is slidably disposed through an inner lumen of the insertion device.
Figure 5E:
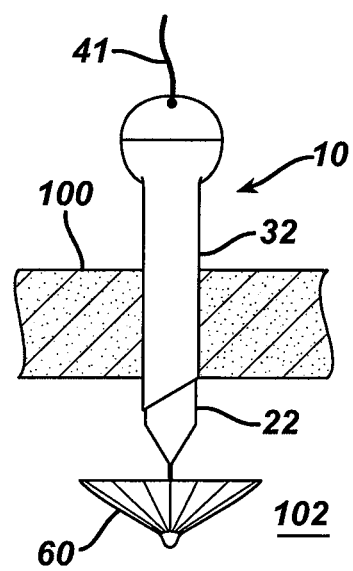
FIG. 5E is a representation of the retraction mechanism of FIG. 5A being moved from an extended position to a retracted position thereby exerting a pulling force on the tissue wall while also acting as a shield between the internal organs and the distal end of the insertion device.

In use, the distal portion of the retraction mechanism 42 can be initially positioned into the body cavity (e.g., via any type of delivery device such as an insertion needle), and a proximal portion 41 of the mechanism 40, which can be an actuation cord, can be slidably disposed within the inner lumen of the elongate sleeve 22 thereby allowing the distal end 42 of the mechanism to pull the cavity wall towards the distal end 26 of the sleeve 22 as will be discussed below. As such, the ability of the retraction mechanism 40 to pull the cavity wall into contact with the sleeve 22 substantially eliminates the need to push the insertion device 10 into the target cavity thereby significantly reducing the potential for injury resulting from over-insertion of the device 10. As will be discussed in detail below, the device 10 can be configured in various ways so as to facilitate delivery across the cavity wall. For example, the distal portion 26 the elongate sleeve 22 (and outer cannula 30, if present) can be tapered and/or include various protrusions configured to pass through tissue. Additionally, the insertion device 10 can include various configurations of a blade(s) 50 disposed at various locations of the device 10. For example, as shown in FIGS. 3A-3C, the blade (s) 50 can be positioned within the inner lumen of the elongate sleeve 22 such that the blade(s) 50 is shielded from the treatment site by the elongate sleeve 22 thereby requiring the cavity wall 100 to be pulled into contact with the blade(s) 50. In other embodiments, as shown in FIGS. 4A-4B, the blade(s) 50 can be disposed on the distal portion 42 of the retraction mechanism 40 thereby allowing for the blade(s) 50 to be pulled (again, not pushed) into contact with the cavity wall 100. In alternative embodiments, the distal portion 42 of the retraction mechanism 40 can be further configured to provide a shield element 60 (see FIGS. 5A-5E) capable of shielding internal organs from the distal portion 26 of the sleeve 22 upon insertion into the cavity.

As mentioned, the insertion device 10 includes an elongate sleeve 22 configured for passage across a body cavity wall 100. As will be apparent to those skilled in the art, the elongate sleeve 22 can be virtually any type of sleeve or sleeve-like device configured to provide access across the cavity wall 100. As shown in FIG. 1B, the elongate sleeve 22 includes a proximal end 22a that can be coupled to a housing 24, a distal end 26 with an opening 26o, and an inner lumen extending therebetween such that the inner lumen is in communication with the distal opening 26o and a proximal opening (not shown). As will be described in detail below, the inner lumen is configured to slidably receive a tissue retraction mechanism 40 which extends from the distal end of the sleeve 26, which upon deployment engages an inner portion of the cavity wall 100 and pulls the cavity wall 100 into contact with the distal end 26 of the elongate sleeve 22 as the retraction mechanism 40 is slid proximally relative to the sleeve 22.

The distal tip 26 of the elongate sleeve 22 can include various configurations capable of facilitating passage of the sleeve 22 through the cavity wall 100 as the wall 100 is pulled into contact with the sleeve 22 via the retraction mechanism 40. For example, as shown in FIG. 1B, a portion of the distal end 26 of the elongate sleeve 22 can be tapered. In other embodiments, the distal end 26 of the sleeve 22 can include various protrusions (not shown) which are also configured to facilitate passage of the sleeve 22 through the wall 100. In other embodiments, the distal end 26 of the elongate sleeve 22 can be substantially blunt. As will be discussed below, a blunt distal end 26 can be especially useful in those embodiments utilizing a blade 50 disposed on the distal portion 42 of the retraction mechanism 40 so that the cavity wall 100 can be positioned between the blade 50 and the blunt end 26 of the device 10 thereby allowing the wall 100 to be squeezed therebetween. Those skilled in the art will appreciate that virtually any such configuration of the distal end 26 of the elongate sleeve 22 is within the spirit and scope of the present invention.

In one embodiment, the insertion device 10 can also include an outer cannula 32 (e.g., a trocar sheath), which is shown in more detail in FIG. 1C. While the outer cannula 32 can have virtually any configuration, it preferably includes a hollow shaft that is configured to be slidably disposed over the elongate sleeve 22. The size of the outer cannula 32 can vary, but it preferably has a length that is slightly less than a length of the elongate sleeve 22 such that the tip 26 of the elongate sleeve 22 extends distally beyond a distal end 32b of the cannula 32. The diameter can also vary, but as indicated above, the diameter should be sufficient to allow the outer cannula 32 to receive the elongate sleeve 22 therein. Further, as will be discussed below, the diameter of the outer cannula 32 should also be sufficient to allow passage of the distal end 42 of the retraction mechanism 40 as the retraction mechanism 40 is withdrawn from the treatment site.

Similar to the elongate sleeve 22, the outer cannula 32 can also include various features to facilitate use of the cannula 32 with the elongate sleeve 22, and also to facilitate passage of a distal portion 32b of the cannula 32 through the cavity wall. For example, the distal end 32b of the outer cannula 32 can have an outer diameter that tapers distally, as shown, to form a substantially smooth continuous transition from the outer cannula 32 to the tip 26 of the elongate sleeve 22. Similarly, the outer cannula 32 can also include a housing 34 formed on or coupled to a proximal end 32a of the elongate shaft. In some embodiments, these housings 24, 34 can be configured to releasably engage one another. In other embodiments, the housings 24, 34 can include various seals (not shown) which are configured to provide a substantially closed environment during various surgical procedures. As will be apparent to those skilled in the art, various configurations of such housings 24, 34 are within the spirit and scope of the present invention. For example, various embodiments of housings 24, 34 configured for use with the elongate sleeve 22 and/or outer cannula 32 are provided in assignee's co-pending patent application, U.S. patent application Ser. No. 11/382,173, filed on May 8, 2006, the entirety of which is incorporated herein by reference.

As mentioned above, the insertion device 10 further includes a tissue retraction mechanism 40 configured to pull the cavity wall 100 into contact with the distal portion 26 of the elongate sleeve 22 thereby eliminating the need to drive the device 10 into the body cavity via a pushing force. As such, the retraction mechanism 40 can be any mechanism configured to be slidably disposed within the inner lumen of the elongate sleeve 22, and further configured to pull the cavity wall towards the distal end 26 of the elongate sleeve 22 as a retraction force (F) is supplied to the retraction mechanism 40. In an exemplary embodiment, the tissue retraction mechanism 40 includes a retraction element 41, such as an actuation cord, that extends between a proximal end 41a and a distal end 41b which is coupled to a tissue engagement element 42, e.g., at a mid-portion thereof. The retraction element 41 can be any element configured to extend through the inner lumen of the sleeve 22, and further configured, as will be discussed below, to apply a pulling force to the tissue engagement element 42. For example, the retraction element 41 can be a cord such as a suture, a wire, a fiber, a cable, etc. Those skilled in the art will appreciate that the retraction element 41 can be of any diameter which allows the element 41 to be slidably disposed within the inner lumen of the elongate sleeve 22. Also, while the retraction element 41 can be of any length, typically, the retraction element 41 should be long enough such that the element 41 can extend through the entire inner lumen of the sleeve 22. Additionally, the retraction element 41 should be long enough such that the retraction element 41 can extend across the body cavity wall 100 and into the body cavity 102, and the element 41 should also extend from the proximal opening of the elongate sleeve 22 thereby allowing a retraction force (F) to be supplied (manually or via any type of mechanical actuator) to a proximal portion 41a of the retraction element 41. As discussed below, the retraction force (F) can be any force capable of pulling the wall of the body cavity towards the distal end 26 of the elongate sleeve 22. Additionally, the retraction force can be supplied to any portion of the retraction element 41 capable of translating the retraction force to the distal end 42 of the mechanism 40.

As mentioned above, in an exemplary embodiment, the distal end of the tissue retraction mechanism 40 includes a tissue engagement element 42 coupled to the distal end 41b of the retraction element 41. The tissue engagement element 42 can be virtually any element configured to supply a pulling force to the body cavity wall as the tissue retraction mechanism 40 is moved proximally (e.g., from an extended position to a retracted position). In an exemplary embodiment, the tissue engagement element 42 is an elongate element such as a T-tag. While the tissue engagement element 42 can be virtually any size or shape, the element 42 should be configured to pass through the inner lumen of the elongate sleeve 22 and/or the outer cannula 32 such that the tissue retraction mechanism 40 can be withdrawn from the treatment site following insertion of the device 10 into the cavity. For example, the diameter of the tissue engagement element 42 can be configured to be smaller than the diameter of the inner lumen of the sleeve 22 and/or cannula 32. Alternately, the tissue engagement element 42 can be manipulated (e.g., turned sideways, inverted, etc.) upon introduction to the inner lumen. In one embodiment, the tissue engagement element 42 can be configured in a delivery orientation in which it is aligned with a longitudinal axis of the sleeve 22, cannula 32, and/or a delivery device. In a deployed orientation, the tissue engagement element 42 can be oriented transverse to a longitudinal axis of the sleeve 22 such that it cannot pass through the lumen. Those skilled in the art will appreciate that various such manners of manipulating the tissue engagement element 42 are well known in the art, and clearly within the spirit and scope of the present invention.

Figure 2A:
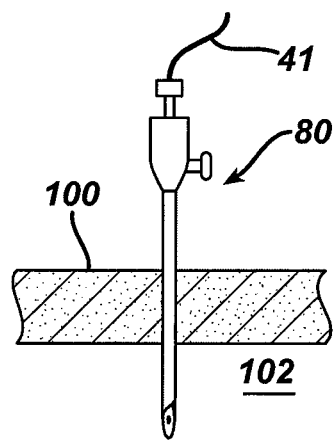
FIG. 2A is a representation of a distal end of an embodiment of the retraction mechanism being positioned across a body cavity wall via an insertion needle.
Figure 2B:
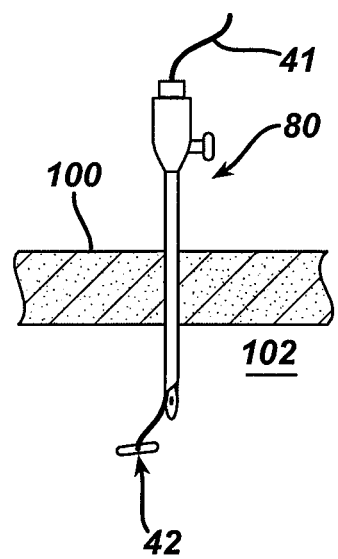
FIG. 2B is a representation of the distal end of the retraction mechanism of FIG. 2A being deployed from the insertion needle into the body cavity.
Figure 2C:
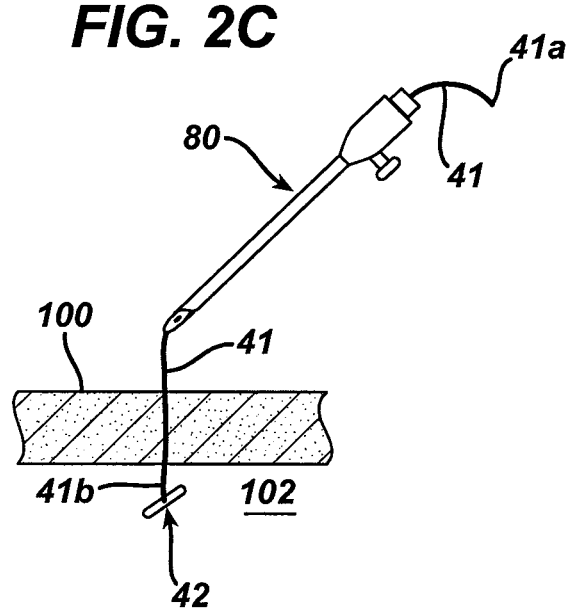
FIG. 2C is a representation of the insertion needle of FIG. 2A being withdrawn from the treatment site.
Figure 2D:
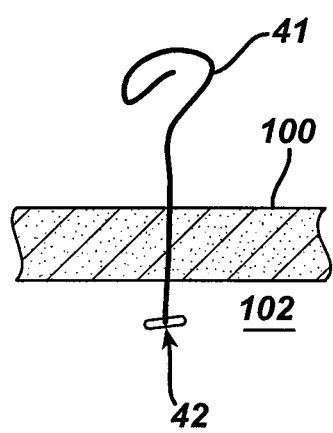
FIG. 2D is a representation of the retraction mechanism of FIG. 2A being disposed across the body cavity wall.
Figure 2E:
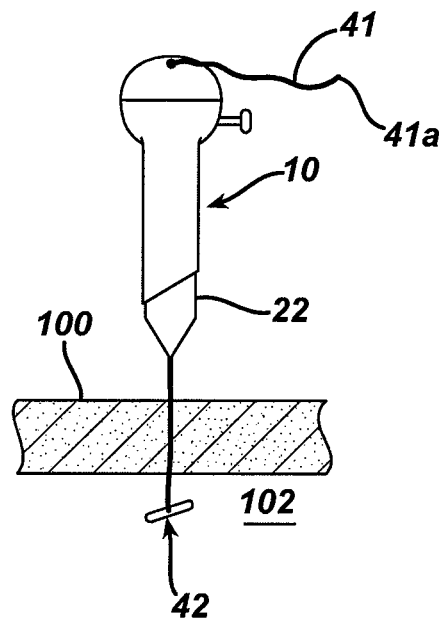
FIG. 2E is a representation of an embodiment of an insertion device receiving a proximal portion of the retraction mechanism of FIG. 2A such that the retraction mechanism is slidably disposed through an inner lumen of the insertion device.
Figure 2F:
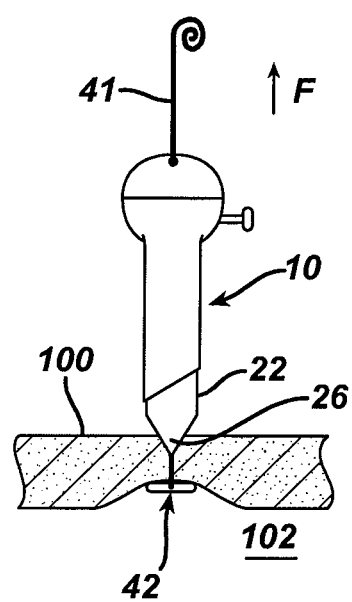
FIG. 2F is a representation of the retraction mechanism of FIG. 2E being moved proximally thereby exerting a pulling force on the tissue wall.

FIGS. 2A-2F provide a representation of an exemplary embodiment of the insertion device 10 in use. As an initial step, shown in FIG. 2A, the distal end 42 of the retraction mechanism 40 (i.e., the tissue engagement element) can disposed within an inner lumen of any type of insertion needle 80 (e.g., a veress needle) thereby allowing the insertion needle 80 to transport the distal end 42 of the retraction mechanism 40 across the cavity wall 100. After the distal portion of the insertion needle 80 has pierced the cavity wall 100, as shown in FIG. 2B, the distal end 42 of the retraction mechanism 40 can be deployed from the insertion needle 80 by any of a wide range of various mechanisms known to those skilled in the art. Next, as shown in FIGS. 2C-2D, the insertion needle 80 can be slid proximally along the retraction mechanism 40 thereby leaving the distal portion 42 of the retraction mechanism 40 (i.e., the tissue engagement element) within the body cavity 102, and a portion 41 of the retraction mechanism 40 (i.e., the retraction element) extending through the cavity wall 100 and away from the treatment site. Next, as shown in FIG. 2E, the proximal end 41a of the retraction element 41 is slid into the distal opening 26o at the distal tip 26 of the elongate sleeve 22, through the inner lumen, and out of the proximal opening of the sleeve 22. Once disposed as such, the elongate sleeve 22 can be slid proximally relative to the retraction element 41 thereby positioning the distal end 26 of the sleeve 22 adjacent to the outer portion of the cavity wall 100. At this stage, as shown in FIG. 2F, a retraction force ("F") can be exerted on a proximal portion (or any portion) of the retraction mechanism 41 thereby pulling the distal end 42 of the retraction mechanism 40 into contact with the cavity wall 100. Upon continued retraction, as described above, the distal end 42 of the retraction mechanism 40 can be pull the body cavity wall 100 towards and over the distal end 26 of the elongate sleeve 22. In an exemplary embodiment, the distal opening 26o of the sleeve 22 is configured to allow for the distal portion 42 of the retraction mechanism to pull a portion of the cavity wall therethrough. In those embodiments utilizing an outer cannula 32, the distal opening 26o and/or distal end 26 of the sleeve 22 can be configured to engage the distal end 42 (e.g., in a slot, a groove, a bore, etc.) such that the retraction mechanism 40 and the elongate sleeve 22 can easily be withdrawn from the cannula 32. As such, after the distal end 26 of the sleeve 22 has been positioned across the cavity wall 100, the retraction mechanism 40 can be withdrawn from the treatment site by sliding the retraction mechanism 40 through the inner lumen and out of the elongate sleeve 22. As mentioned, in those embodiments having an outer cannula 32, the elongate sleeve 22 and retraction mechanism 40 can be withdrawn from the cavity 102 thereby leaving the cannula 32 in position to provide access to the treatment site 102.

Various embodiments of the insertion device 10 can include at least one blade 50 configured to facilitate passage of the device 10 through the cavity wall 100. In general, the blade(s) 50 can be disposed such that the cavity wall 100 must be pulled into the blade 50, or the blade 50 is pulled proximally through the wall 100 (i.e., away from internal organs) thereby preventing the blade(s) 50 from being pushed through the cavity wall 100 and potentially into contact with various internal organs. FIGS. 3A-3C provide one exemplary embodiment of a such a bladed insertion device 10. As shown in FIG. 3A, the blade 50 can be fixedly coupled within the inner lumen of the elongate sleeve 22 at a position which is proximal of the distal end 26 of the sleeve 22. In such a configuration, the elongate sleeve 22 can effectively shield tissue from the blade 50. Therefore, as shown in FIG. 3B, the distal opening of the sleeve 22 can be configured as a slot 29 such that the distal end 42 of the retraction mechanism 40 can pull a portion of the cavity wall 100 into the inner lumen (FIG. 3C), and into communication with the blade 50 which thereby facilitates passage of the sleeve 22 through the wall 100. Like above, following insertion of the distal end 26 of the sleeve 22, the elongate sleeve 22 and retraction mechanism 40 can be withdrawn from the treatment site 102, and the outer cannula 32 can remain in place.

In another embodiments, the blade(s) 50 can be incorporated into the distal end 42 of the retraction mechanism 40 thereby allowing the blade 50 to be pulled through the cavity wall 100 which again prevents the blade 50 from being driven through the wall 100. Those skilled in the art will appreciate that blades 50 of various sizes, shapes, and/or configurations can be incorporated in various manners into/onto the distal end 42 of the retraction mechanism 40. In the exemplary embodiment of FIGS. 4A-4B, the distal end 42 of the retraction mechanism 40 includes a deployable blade 50 configured to enter the body cavity 102 in an undeployed state (FIG. 4A), and configured to be manipulated to a deployed state (FIG. 4B). Those skilled in the art will appreciate that various mechanisms can be utilized to deploy the blade(s) 50. For example, as shown in FIG. 4A, the retraction mechanism 40 can once again include a retraction element 41 configured to apply the pulling force to the distal end 42 of the retraction mechanism, and a second element 41' ("a hold element") configured to retain the blade 50 in an undeployed state (e.g., within a housing 44 of the tissue engagement element 42). As will be shown, the hold element 41' can be any element configured to be cut by the blade 50 as the blade is forced against the element 41'. For example, the hold element 41' can be a suture. As such, and with reference to FIG. 4B, an initial proximal force supplied by the retraction element 41 and the hold element 41' move the distal portion 42 of the retraction mechanism 40 proximally and into contact with the cavity wall. An additional force supplied to the elements 41, 41' (such force now being met with resistance from the wall 100) results in the retraction element 41 pulling the blade 50 against the hold element 41' thereby cutting the hold element 41'. Once the hold element 41' is cut, the blade 50 can move from an undeployed position to a deployed position. As shown, the retraction element 41 can couple the blade 50 at a central hinge 52 thereby allowing the blade 50 to adopt a substantially inverted "V" shape as the distal end 42 of the retraction mechanism 40 is pulled into the cavity wall 100. As mentioned above, various other blade configurations or deployment mechanisms are within the spirit and scope of the present invention.

In other embodiments, in addition to exerting a pulling force on the cavity wall 100, the distal end 42 of the retraction mechanism 40 can also be configured to shield the internal organs from the distal end 26 of the sleeve 22 as the elongate sleeve 22 is delivered through the cavity wall 100. As shown in FIGS. 5A-5E, upon introduction to the body cavity 102 (again, via some type of insertion needle 80), the distal end 42 of the retraction mechanism 40 can be deployed as a shield element 60. In general, the shield element 60 can be any element capable of blocking the distal end 26 of the elongate sleeve 22 from the internal organs. For example, as shown, the shield element 60 can be configured as an inverted-dome or similar such structure wherein the element 60 can be formed of various biocompatible materials (e.g., polymers, etc.) Furthermore, following insertion of the sleeve 22 through the cavity wall 100 (FIG. 5E), the shield element 60 can remain adjacent the distal end 26 of the sleeve 22 as the sleeve 22 approaches the treatment site (e.g., the organ) thereby shielding the site from the distal tip 26 of the sleeve 22 until the sleeve 22 is properly positioned. Once positioned, the element 60 can be withdrawn from the cavity 102 through the inner lumen of the sleeve 22 via a retraction force supplied to the retraction mechanism 40. As will be apparent to those skilled in the art, to allow removal, the shield element 60 can be manipulated from the deployed state to an undeployed state by any number of mechanisms (e.g., inverting the element 60, incorporating a second suture to close the element 60, etc). All such mechanisms are within the spirit and scope of the present invention.

Additionally, methods for providing access to a body cavity (e.g., the abdominal cavity) are also provided herein. In general, the method allows for a cavity wall to be pulled into and over the distal end of an elongate sleeve as opposed to driving the device through the cavity wall. The method can include accessing any body cavity as required by any given procedure. In an exemplary embodiment, the body cavity is the abdomen, and the method provides access to the abdomen across the peritoneum. As such, in an exemplary embodiment, the method includes disposing a distal portion of a retraction mechanism across a wall of a body lumen (e.g., via an insertion needle) and slidably disposing a portion of the retraction mechanism within an inner lumen of an elongate sleeve of the device. As described above, the distal portion of the retraction mechanism can be configured so as to securely engage the cavity wall so as to pull the wall towards the distal end of the device in response to a retraction force. As such, the method further includes supplying a retraction force to the retraction mechanism so as to pull the cavity wall towards and over the distal end of the sleeve thereby positioning the sleeve across the cavity wall. Optionally, the method can include providing insufflation to the target cavity so as to further facilitate accessing the cavity.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An insertion device, comprising:
   an outer cannula having a lumen extending therethrough;
   an elongate sleeve having an inner lumen extending therethrough, the elongate sleeve having an outer diameter less than an inner diameter of the lumen of the outer cannula so that the elongate sleeve can be slidably disposed within the outer cannula; and
   a tissue retraction mechanism slidably disposed within the inner lumen of the elongate sleeve, the tissue retraction mechanism configured to extend from a distal end of the sleeve and be temporarily deployed through tissue and into a body cavity in advance of the elongate sleeve and outer cannula, and removed from the tissue after the outer cannula has been deployed through at least one layer of tissue, the tissue retraction mechanism having a distal end member configured to move from a delivery configuration to a deployed configuration in which the tissue retraction mechanism is oriented so as to be substantially perpendicular to a longitudinal axis of the elongate sleeve without changing shape and to engage tissue and apply a pulling force to the tissue as the tissue retraction mechanism is moved proximally;
   wherein the outer cannula has a diameter sufficient to allow passage of the distal end of the retraction mechanism in the deployed configuration as the retraction mechanism is withdrawn through the outer cannula.

2. The device of claim 1, further comprising a blade disposed within the sleeve.

3. The device of claim 1, wherein the distal end member of the tissue retraction mechanism includes a blade configured to be manipulated from an undeployed state to a deployed state.

4. The device of claim 1, wherein the tissue retraction mechanism includes an actuating cord configured to extend beyond a proximal end of the sleeve.

5. The device of claim 4, wherein the distal end member is an elongate, rod-like member, the actuating cord includes a distal end attached to a mid-portion of the elongate member, and the elongate member is configured to engage tissue and apply a pulling force to the tissue as the actuating cord is moved proximally.

6. The device of claim 1, wherein the elongate sleeve is an obturator.

7. A trocar device, comprising:
a hollow outer cannula;
an elongate sleeve having an inner lumen extending therethrough, the elongate sleeve being removeably and replaceably disposable within the outer cannula, and the elongate sleeve and the outer cannula being configured so that a distal end of the elongate sleeve contacts tissue before a distal end of the outer cannula;
a retraction element comprising a flexible member slidably disposed within the inner lumen of the elongate sleeve, at least a portion of the retraction element configured to extend from the distal end of the sleeve; and
a tissue engagement element coupled to a distal end of the retraction element, the tissue engagement element configured to apply a pulling force to a tissue as the retraction element is moved in a proximal direction and to be removed from the tissue in a deployed configuration after the outer cannula has been deployed through at least one layer of tissue, wherein in the deployed configuration the tissue retraction mechanism is oriented so as to be substantially perpendicular to a longitudinal axis of the elongate sleeve.

8. The device of claim 7, wherein the retraction element is a suture.

9. The device of claim 7, further comprising a blade disposed within the sleeve.

10. The device of claim 7, wherein the tissue engagement element is an elongate member and the retraction element is coupled to a mid-portion thereof, the elongate member being configured to be oriented perpendicular to a longitudinal axis of the sleeve as the elongate member applies a pulling force to a tissue.

11. The device of claim 7, wherein the tissue engagement element includes a blade.

12. The device of claim 11, wherein the blade is configured to be manipulated from an undeployed state to a deployed state.

13. The device of claim 7, wherein the elongate sleeve is an obturator.

14. The device of claim 7, wherein the tissue engagement element is further configured to include a shield element, the shield element being configured to be deployed so as to adopt an inverted dome configuration.

15. A method of providing access to a body cavity, comprising:
delivering a distal end of a tissue retraction mechanism of an insertion device across a body cavity wall to a deployed configuration;
positioning a proximal portion of the tissue retraction mechanism through an inner lumen of an elongate sleeve, the tissue retraction mechanism configured to be axially movable relative to the sleeve;
positioning the distal end of the sleeve adjacent to an outer portion of the body cavity wall;
retracting the proximal portion of the tissue retraction mechanism such that the distal end of the tissue retraction mechanism pulls the wall of the body cavity toward the distal end of the elongate sleeve and the distal end of the elongate sleeve passes through the body cavity wall; and
removing the tissue retraction mechanism from within the body cavity wall in the deployed configuration after the elongate sleeve passes through the body cavity wall, wherein in the deployed configuration the tissue retraction mechanism is oriented so as to be substantially perpendicular to a longitudinal axis of the elongate sleeve.

16. The method of claim 15, wherein the body cavity is the abdomen.

17. The method of claim 16, wherein the wall of the body cavity is the peritoneum.

* * * * *